US012781210B2

(12) United States Patent
Wang et al.

(10) Patent No.: US 12,781,210 B2
(45) Date of Patent: Nov. 3, 2026

(54) GENE FOR EFFICIENTLY EXPRESSING HYALURONIC ACID HYDROLASE AND EXPRESSION METHOD THEREOF

(71) Applicant: BLOOMAGE BIOTECHNOLOGY CORPORATION LIMITED, Shandong (CN)

(72) Inventors: Hao Wang, Shandong (CN); Tianmeng Zhang, Shandong (CN); Rongrong Xu, Shandong (CN); Youheng Zhang, Shandong (CN); Xueping Guo, Shandong (CN); Jingkun Hao, Shandong (CN)

(73) Assignee: BLOOMAGE BIOTECHNOLOGY CORPORATION LIMITED, Shandong (CN)

( * ) Notice: Subject to any disclaimer, the term of this patent is extended or adjusted under 35 U.S.C. 154(b) by 565 days.

(21) Appl. No.: 18/280,403

(22) PCT Filed: Mar. 23, 2021

(86) PCT No.: PCT/CN2021/082346
§ 371 (c)(1),
(2) Date: Sep. 5, 2023

(87) PCT Pub. No.: WO2022/183542
PCT Pub. Date: Sep. 9, 2022

(65) Prior Publication Data

US 2024/0150742 A1 May 9, 2024

(30) Foreign Application Priority Data

Mar. 5, 2021 (CN) ......................... 202110246672.0

(51) Int. Cl.
*C12N 9/26* (2006.01)
*C12N 1/165* (2026.01)
*C12R 1/84* (2006.01)

(52) U.S. Cl.
CPC ........... *C12N 9/2474* (2013.01); *C12N 1/165* (2021.05); *C12N 2500/30* (2013.01); *C12N 2523/00* (2013.01); *C12R 2001/84* (2021.05)

(58) Field of Classification Search
None
See application file for complete search history.

(56) References Cited

FOREIGN PATENT DOCUMENTS

| | | |
|---|---|---|
| CN | 1366049 | 8/2002 |
| CN | 103436508 | 12/2013 |
| CN | 103614352 | 3/2014 |
| CN | 104263707 | 1/2015 |
| CN | 108064282 | 5/2018 |
| CN | 108291245 | 7/2018 |
| CN | 108949603 | 12/2018 |
| CN | 110621778 | 12/2019 |
| CN | 110713983 | 1/2020 |
| CN | 110951714 | 4/2020 |
| WO | 2016/061286 | 4/2016 |
| WO | 2017/007907 | 1/2017 |
| WO | 2018/169750 | 9/2018 |

OTHER PUBLICATIONS

Reitinger, S., et al. 2008 Protein Expression and Purification 57: 226-233. (Year: 2008).*
Invitrogen EasySelect™ Pichia Expression Kit User Manual 2010: 95 pages. (Year: 2010).*
Zhang, W., et al. 2005 Biotechnol Prog 21(2): 386-393. (Year: 2005).*
Park, C., et al. 2019 J Microbiol Biotechnol 29(8): 1310-1315. (Year: 2019).*
Block, H., et al. 2009 Methods in Enzymology 463: 439-473. (Year: 2009).*
International Search Report issued Nov. 2, 2021 in International Application No. PCT/CN2021/082346.
Kazuma, K. et al., "TSA: Odontomachus monticola mRNA, Om13456_c0_g1_i1, mRNA sequence", GenBank: FX985505.1, Feb. 5, 2019, 2 pages.
Konorov, E.A. et al., glycylpeptide n-tetradecanoyltranferase 1-like protein [Lasius niger], Genbank: KMQ98097.1, Jul. 2, 2015, 2 pages.

* cited by examiner

*Primary Examiner* — Marsha Tsay
(74) *Attorney, Agent, or Firm* — Wenderoth, Lind & Ponack, L.L.P.

(57) ABSTRACT

Provided is a gene for efficiently expressing hyaluronic acid hydrolase. A nucleotide sequence of the gene is represented by SEQ ID NO: 4. By truncating a segment of a signal peptide sequence at the N-terminus of a full-length hyaluronic acid hydrolase gene, the *Pichia pastoris* engineering strain of high level expression genetic engineering hyaluronic acid hydrolase is constructed. The enzyme activity of the hyaluronic acid hydrolase in a fermentation broth obtained by high-density fermentation using the constructed *Pichia pastoris* engineering strain is up to $4.7\times10^5$ U/mL.

17 Claims, 3 Drawing Sheets

Specification includes a Sequence Listing.

SEQ ID NO. 8
SEQ ID NO. 1

SEQUENCE LISTING

```
<160> NUMBER OF SEQ ID NOS: 8

<210> SEQ ID NO 1
<211> LENGTH: 1074
<212> TYPE: DNA
<213> ORGANISM: Artificial sequence
<220> FEATURE:
<223> OTHER INFORMATION: Description of Artificial Sequence:
      artificially synthesized sequence

<400> SEQUENCE: 1

atgatcccac ccgcacgtga ctcgcttatg tttgtctttg cgactgcggt aatcgctagt      60

tttttcggta gcgcaaagac actacgcggc tcttccccac agcaattcga cgtatactgg     120

aatgtgccaa ctttcatgtg tcacaagcac ggtatgaaat ttgaagagct gaaagatttc     180

ggtatacacc agaacgcaat ggatatgttt cgcggcgaag aaattgcgat tctttatgac     240

cctggcatgt ttcccgccct tctagtagat aaagatggat acgtcactaa acggaacggt     300

ggggtgccgc aagaggggaa cctcaaggaa catttagaaa cctttagaaa gcatctgacg     360

acacaaattc cggacgagag ctttagcggg ataggaatca tagactttga gagttggaga     420

ccgattttca ggcagaactg ggcgtcactc gagccctata aactttgtc cataaagttg      480

gagagggaaa aacacccatt ttggtcggag gcagctgtga agaaggaggc caaacgtcga     540

ttcgagaaat ccgggcgaat atttatggag gaaaccctca aaatggccaa aaaactaaga     600

ccgaaagcaa agtggggcta ttatgggtat ccccactgtt tcaatcaaac ccctggacag     660

cagtcggttc actgcaatcg gcaaacgatg atggaaaatg acggtatgag ttggctgttt     720

acactcgaag acgttcatgc tcccagcgtt tacctacgat tggaaatcaa ggaggatgac     780

cggccttcat tcgtgaaagg ccgggtttcc gaggccttaa ggttagccgc taaatcgtct     840

tcaaaacaac gtatcctacc ttactactgg ttcatttatc aggataagaa ggatgagttc     900

ttaacggaaa aggatacaca aaacactata aatatgatcg ctaatctggg atctaatggt     960

ttcataattt ggggatctag tgacgatgtc aacacggaac gcaaatgcaa ggatttacag    1020

caatacgtaa aggaagtctt gggcccagcg attaagaagt tcacccttca ttga          1074
```

<210> SEQ ID NO 2
<211> LENGTH: 357
<212> TYPE: PRT
<213> ORGANISM: Artificial sequence
<220> FEATURE:
<223> OTHER INFORMATION: Description of Artificial Sequence:
artificially synthesized sequence

<400> SEQUENCE: 2

```
Met Ile Pro Pro Ala Arg Asp Ser Leu Met Phe Val Phe Ala Thr Ala
1               5                   10                  15

Val Ile Ala Ser Phe Phe Gly Ser Ala Lys Thr Leu Arg Gly Ser Ser
            20                  25                  30

Pro Gln Gln Phe Asp Val Tyr Trp Asn Val Pro Thr Phe Met Cys His
        35                  40                  45

Lys His Gly Met Lys Phe Glu Glu Leu Lys Asp Phe Gly Ile His Gln
    50                  55                  60

Asn Ala Met Asp Met Phe Arg Gly Glu Glu Ile Ala Ile Leu Tyr Asp
65                  70                  75                  80

Pro Gly Met Phe Pro Ala Leu Leu Val Asp Lys Asp Gly Tyr Val Thr
                85                  90                  95

Lys Arg Asn Gly Gly Val Pro Gln Glu Gly Asn Leu Lys Glu His Leu
            100                 105                 110

Glu Thr Phe Arg Lys His Leu Thr Thr Gln Ile Pro Asp Glu Ser Phe
        115                 120                 125

Ser Gly Ile Gly Ile Ile Asp Phe Glu Ser Trp Arg Pro Ile Phe Arg
    130                 135                 140

Gln Asn Trp Ala Ser Leu Glu Pro Tyr Lys Thr Leu Ser Ile Lys Leu
145                 150                 155                 160

Glu Arg Glu Lys His Pro Phe Trp Ser Glu Ala Ala Val Lys Lys Glu
                165                 170                 175

Ala Lys Arg Arg Phe Glu Lys Ser Gly Arg Ile Phe Met Glu Glu Thr
            180                 185                 190

Leu Lys Met Ala Lys Lys Leu Arg Pro Lys Ala Lys Trp Gly Tyr Tyr
        195                 200                 205

Gly Tyr Pro His Cys Phe Asn Gln Thr Pro Gly Gln Gln Ser Val His
    210                 215                 220

Cys Asn Arg Gln Thr Met Met Glu Asn Asp Gly Met Ser Trp Leu Phe
225                 230                 235                 240

Thr Leu Glu Asp Val His Ala Pro Ser Val Tyr Leu Arg Leu Glu Ile
                245                 250                 255

Lys Glu Asp Asp Arg Pro Ser Phe Val Lys Gly Arg Val Ser Glu Ala
            260                 265                 270

Leu Arg Leu Ala Ala Lys Ser Ser Ser Lys Gln Arg Ile Leu Pro Tyr
        275                 280                 285

Tyr Trp Phe Ile Tyr Gln Asp Lys Lys Asp Glu Phe Leu Thr Glu Lys
    290                 295                 300

Asp Thr Gln Asn Thr Ile Asn Met Ile Ala Asn Leu Gly Ser Asn Gly
305                 310                 315                 320

Phe Ile Ile Trp Gly Ser Ser Asp Asp Val Asn Thr Glu Arg Lys Cys
                325                 330                 335

Lys Asp Leu Gln Gln Tyr Val Lys Glu Val Leu Gly Pro Ala Ile Lys
            340                 345                 350

Lys Phe Thr Leu His
```

355

<210> SEQ ID NO 3
<211> LENGTH: 72
<212> TYPE: DNA
<213> ORGANISM: Artificial sequence
<220> FEATURE:
<223> OTHER INFORMATION: Description of Artificial Sequence:
artificially synthesized sequence

<400> SEQUENCE: 3
atcccacccg cacgtgactc gcttatgttt gtctttgcga ctgcggtaat cgctagtttt 60
ttcggtagcg ca 72

<210> SEQ ID NO 4
<211> LENGTH: 1020
<212> TYPE: DNA
<213> ORGANISM: Artificial sequence
<220> FEATURE:
<223> OTHER INFORMATION: Description of Artificial Sequence:
artificially synthesized sequence

<400> SEQUENCE: 4
atgaagacac tacgcggctc ttccccacag caattcgacg tatactggaa tgtgccaact 60
ttcatgtgtc acaagcacgg tatgaaattt gaagagctga aagatttcgg tatacaccag 120
aacgcaatgg atatgtttcg cggcgaagaa attgcgattc tttatgaccc tggcatgttt 180
cccgcccttc tagtagataa agatggatac gtcactaaac ggaacggtgg ggtgccgcaa 240
gaggggaacc tcaaggaaca tttagaaacc tttagaaagc atctgacgac acaaattccg 300
gacgagagct ttagcgggat aggaatcata gactttgaga gttggagacc gattttcagg 360
cagaactggg cgtcactcga gccctataaa actttgtcca taaagttgga gagggaaaaa 420
cacccatttt ggtcggaggc agctgtgaag aaggaggcca aacgtcgatt cgagaaatcc 480
gggcgaatat ttatggagga aaccctcaaa atggccaaaa aactaagacc gaaagcaaag 540
tggggctatt atgggtatcc ccactgtttc aatcaaaccc ctggacagca gtcggttcac 600
tgcaatcggc aaacgatgat ggaaaatgac ggtatgagtt ggctgtttac actcgaagac 660
gttcatgctc ccagcgttta cctacgattg gaaatcaagg aggatgaccg gccttcattc 720
gtgaaaggcc gggtttccga ggccttaagg ttagccgcta aatcgtcttc aaaacaacgt 780
atcctacctt actactggtt catttatcag gataagaagg atgagttctt aacggaaaag 840
gatacacaaa acactataaa tatgatcgct aatctgggat ctaatggttt cataatttgg 900
ggatctagtg acgatgtcaa cacggaacgc aaatgcaagg atttacagca atacgtaaag 960
gaagtcttgg gcccagcgat taagaagttc acccttcatc accaccatca tcatcattga 1020

<210> SEQ ID NO 5
<211> LENGTH: 339
<212> TYPE: PRT
<213> ORGANISM: Artificial sequence
<220> FEATURE:
<223> OTHER INFORMATION: Description of Artificial Sequence:
artificially synthesized sequence

<400> SEQUENCE: 5

Met Lys Thr Leu Arg Gly Ser Ser Pro Gln Gln Phe Asp Val Tyr Trp
1 5 10 15

Asn Val Pro Thr Phe Met Cys His Lys His Gly Met Lys Phe Glu Glu
20 25 30

Leu Lys Asp Phe Gly Ile His Gln Asn Ala Met Asp Met Phe Arg Gly
35 40 45

Glu Glu Ile Ala Ile Leu Tyr Asp Pro Gly Met Phe Pro Ala Leu Leu
50 55 60

Val Asp Lys Asp Gly Tyr Val Thr Lys Arg Asn Gly Gly Val Pro Gln
65 70 75 80

Glu Gly Asn Leu Lys Glu His Leu Glu Thr Phe Arg Lys His Leu Thr
85 90 95

Thr Gln Ile Pro Asp Glu Ser Phe Ser Gly Ile Gly Ile Ile Asp Phe
100 105 110

Glu Ser Trp Arg Pro Ile Phe Arg Gln Asn Trp Ala Ser Leu Glu Pro
115 120 125

Tyr Lys Thr Leu Ser Ile Lys Leu Glu Arg Glu Lys His Pro Phe Trp
130 135 140

Ser Glu Ala Ala Val Lys Lys Glu Ala Lys Arg Arg Phe Glu Lys Ser
145 150 155 160

Gly Arg Ile Phe Met Glu Glu Thr Leu Lys Met Ala Lys Lys Leu Arg
165 170 175

Pro Lys Ala Lys Trp Gly Tyr Tyr Gly Tyr Pro His Cys Phe Asn Gln
180 185 190

Thr Pro Gly Gln Gln Ser Val His Cys Asn Arg Gln Thr Met Met Glu
195 200 205

Asn Asp Gly Met Ser Trp Leu Phe Thr Leu Glu Asp Val His Ala Pro
210 215 220

Ser Val Tyr Leu Arg Leu Glu Ile Lys Glu Asp Asp Arg Pro Ser Phe
225 230 235 240

Val Lys Gly Arg Val Ser Glu Ala Leu Arg Leu Ala Ala Lys Ser Ser
245 250 255

Ser Lys Gln Arg Ile Leu Pro Tyr Tyr Trp Phe Ile Tyr Gln Asp Lys
260 265 270

Lys Asp Glu Phe Leu Thr Glu Lys Asp Thr Gln Asn Thr Ile Asn Met
275 280 285

Ile Ala Asn Leu Gly Ser Asn Gly Phe Ile Ile Trp Gly Ser Ser Asp
290 295 300

Asp Val Asn Thr Glu Arg Lys Cys Lys Asp Leu Gln Gln Tyr Val Lys
305 310 315 320

Glu Val Leu Gly Pro Ala Ile Lys Lys Phe Thr Leu His His His His
325 330 335

His His His

<210> SEQ ID NO 6
<211> LENGTH: 29
<212> TYPE: DNA
<213> ORGANISM: Artificial sequence
<220> FEATURE:
<223> OTHER INFORMATION: Description of Artificial Sequence: artificially synthesized sequence

<400> SEQUENCE: 6
ccggaattca tgaagacact acgcggctc 29

<210> SEQ ID NO 7
<211> LENGTH: 51
<212> TYPE: DNA
<213> ORGANISM: Artificial sequence
<220> FEATURE:
<223> OTHER INFORMATION: Description of Artificial Sequence:

-continued

```
      artificially synthesized sequence

<400> SEQUENCE: 7

atttgcggcc gctcaatgat gatgatggtg gtgatgaagg gtgaacttct t            51


<210> SEQ ID NO 8
<211> LENGTH: 1074
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 8

atgataccac cagctcgaga ctctctgatg tttgtcttcg cgactgctgt gatcgccagt     60

ttcttcggca gtgcaaagac cctcagagga agcagtccac agcagtttga cgtttattgg    120

aacgtgccca ctttcatgtg ccacaagcac ggcatgaaat ttgaggaact caaagatttt    180

ggaattcatc agaatgccat ggacatgttc cgtggtgaag agatcgcgat tctttacgat    240

cccggaatgt ttccggcgtt actggtcgat aaggacggat acgtgacgaa aaggaacggc    300

ggcgtgccgc aagaaggaaa cctgaaggag catctcgaaa cattccggaa gcatttaacc    360

actcagattc ccgacgaatc gttcagcggc attggcataa tagacttcga gagttggcgg    420

cctatcttcc gacaaaattg ggcctctctc gagccctaca agacgctgtc cataaaacta    480

gaacgtgaga agcatcccctt ctggagcgag gcggccgtca agaaggaagc gaagcgtcgt    540

ttcgagaagt ccggcaggat tttcatggag gagactctga agatggcgaa gaagctgcga    600

cctaaggcca agtggggtta ctacggctat ccgcattgct tcaatcagac ccccggccaa    660

caatccgtgc attgcaatcg tcagaccatg atggagaatg acggaatgtc ttggctgttc    720

acgctcgagg acgtgcacgc gccttccgtg tacttgagac tggagatcaa ggaggacgat    780

cggccgagct tcgtgaaggg cagagtgtcg gaggcgctgc ggctggcggc gaagagctcg    840

agcaaacaac ggatcttacc ttattactgg ttcatatacc aagataaaaa agatgaattc    900

ctcaccgaga aagacacgca gaacacgatc aacatgatag ccaacctcgg cagcaacggt    960

tttatcattt ggggtagctc cgatgacgtc aacaccgagc ggaagtgcaa ggatctacaa   1020

cagtacgtga aagaagtcct ggggccggcg ataaagaaat tcaccctgca ttaa         1074
```

GENE FOR EFFICIENTLY EXPRESSING HYALURONIC ACID HYDROLASE AND EXPRESSION METHOD THEREOF

TECHNICAL FIELD

The application belongs to the technical field of genetic engineering, and in particular, relates to a gene for efficiently expressing hyaluronic acid hydrolase and an expression method thereof.

BACKGROUND ART

Hyaluronidase (HAase) is a general term for a class of enzymes that can act on the β-1,3 or β-1,4 glycosidic bond of hyaluronic acid sugar chains to degrade hyaluronic acid, and is widely distributed in nature. Hyaluronidase may be widely applied in clinicas a pharmacologically active substance. For example, it is used in combination with local anesthetics in ophthalmic surgery to speed up the onset of anesthetics. It can promote the diffusion of medicine liquid, exudate or blood stored locally in theeye and the absorption of ocularvitreous opacity, prevent eyeball adhesion after conjunctival chemical burns, and eliminate related inflammatory reactions. Hyaluronic acid filling is an important means of plastic surgery, but hyaluronic acid complications may occur. Hyaluronic acid hydrolase can effectively treat the above adverse reactions as the most effective substance that may be used to hydrolyze hyaluronic acid. Hyaluronidase combined with anti-tumor drugs to assist subcutaneous administration, instead of venipuncture, to improve the medical experience of patients, is currently a hot market application with great potential. In addition, as a tool enzyme, hyaluronidase can efficiently prepare low-molecular-weight hyaluronic acid and hyaluronic acid oligosaccharides, which are more easily absorbed and utilized by the body, and also has huge market prospects in the field of food and cosmetics.

HAases are divided into three types according to differences in their origin, catalytic mechanism and substrate specificity. The first type is hyaluronic acidlyase derived from microorganisms. This type of HAase (EC 4.2.2.1) cleaves the β-1,4glycosidic bond of hyaluronic acid through the β racemization reaction, with the main product being an unsaturated disaccharide molecule 2-acetamido-2-deoxy-3-O-(β-D-gluco-4-enepyranosyluronicacid)-D-glucose. Such hyaluronic acidlyases are mainly derived from *Clostridium, Micrococcus, Streptococcus, Bacillus* and *Streptomyces*. The second type of representative HAase (EC 3.2.1.36) is mainly derived from leech salivary glands and duodenal worms, belongs to endo-β-glucuronidase, and can hydrolyze the β-1,3glycosidic bond of hyaluronic acid with the final product being mainly saturated hyaluronic acidtetrasaccharideand containing a small amount of hyaluronic acidhexasaccharide. This type of HAase has strong substrate specificity and basically does not have hydrolytic and transglycosidic activities on chondroitin sulfate and dermatan sulfate structures. The third type of hyaluronidase is endo-β-N-acetylglucosaminidase (EC 3.2.1.35), is mainly derived from mammalian testis and animal venom, and can hydrolyze β-1,4glycosidic bond of hyaluronic acidwith the final product being mainly hyaluronic acidtetrasaccharide. Such enzymes have a broad substrate spectrum, also have certain catalytic activity on chondroitin sulfate and dermatan sulfate structures, and have transglycosidic activity.

The research on the first type of hyaluronic acidlyase and the second type of endo-β-glucuronidase has been reported in many literatures. Although there are also reports on the third type of endo-β-N-acetylglucosaminidase, the reports mainly focus on the PH20 enzyme derived from mammalian testis, and there are few reports on hyaluronidaseof animal venom. In 2017, KoheiKazuma et al. conducted a complete analysis of the venom components of odontomachusmonticolafor the first time based on transcriptome and peptidomics techniques, and identified a full-length hyaluronic acid hydrolase sequence. At present, there is no relevant report on the recombinant expression of hyaluronic acid hydrolase in odontomachusmonticola.

SUMMARY

In view of the problems existing in the prior art, the present application provides a gene for efficiently expressing hyaluronic acid hydrolase and an expression method thereof.

Specifically, the present application relates to the following aspects:

1. A gene for efficiently expressing hyaluronic acid hydrolase, having a nucleotide sequence as shown in SEQ ID NO.4.

2. A protein encoded by the gene of item 1, having a sequence as shown in SEQ ID NO.5.

3. A recombinant expression vector comprising the nucleotide sequence of item 1.

4. The recombinant expression vector of item 3, wherein a plasmid backbone is the *Pichia pastoris* vector of pPIC series or pGAP series or pAO815, preferably pPIC9K.

5. A *Pichia pastoris*, comprising the expression vector of item 3 or 4.

6. A method for producing hyaluronic acid hydrolase, comprising:

producing the hyaluronic acid hydrolase byusing a recombinant *Pichia pastoris* strain comprisingthe gene of item 1 or the *Pichia pastoris* of item 5.

7. The method of item 6, wherein the *Pichia pastoris* is a strain of GS115, KM71 or SMD1168.

8. The method of item 6, wherein the method comprises producingthe hyaluronic acid hydrolasethrough fermentation by BMMY medium and methanolinduction.

9. The method of item 8, wherein conditions of the fermentation are as follows: fermentation temperature is 25° C.-30° C., and 0.5%-1% (v/v) methanol is supplemented every 24 hours during fermentation process to induce expression for 96 hours.

10. The method of item 6, wherein the method comprises producingthe hyaluronic acid hydrolase through fermentation by BSM medium and methanolinduction.

11. The method of item 10, wherein the method comprises steps of:

inoculatingPichia *pastoris* into a seed medium to obtain a seed liquid;

inoculating the seed liquid into a BSM fermentation medium for fermentation to obtain a fermentation broth containing the hyaluronic acid hydrolase, wherein a fermentation process sequentially comprise four stages: initial fermentation, feeding, starvation culture, and methanol induction.

12. The method of item 11, wherein conditions of the initial fermentation are as follows: fermentation temperature is 25° C.-30° C., and pH is 5-7.

13. The method of item 11, wherein a time of starvation culture is 2-3 hours.

14. The method of item 11, wherein the methanol induction is performed at a temperature of 25° C.-30° C. for 80-120 hours.

15. The method of item 11, wherein the method further comprises purifying the fermentation broth.

16. The method of item 15, wherein the purification is performed by affinity chromatography using nickel column media and gradient elution using 100-500 mM imidazole buffer.

17. Use of the protein of item 2 in the preparation of hyaluronic acid-containing adjuvants, foods and cosmetics.

In the present application, a *Pichia pastoris* engineering strain expressing a high level of genetically engineered hyaluronic acid hydrolase is constructed by truncating a segment of a signal peptide sequence at the N-terminus of the full-length hyaluronic acid hydrolase gene. The enzymatic activity of hyaluronic acid hydrolase in the fermentation broth obtained by high-density fermentation using the constructedPichia *pastoris* engineering strainisup to $4.7\times10^5$U/mL. Therefore, it will be beneficial to further reduce the cost of industrial production of the hyaluronic acid hydrolase of odontomachusmonticola, thereby expanding the application scope of the hyaluronidase in the fields of medicine, chemical industry and food.

DETAILED DESCRIPTION

Figure 1:
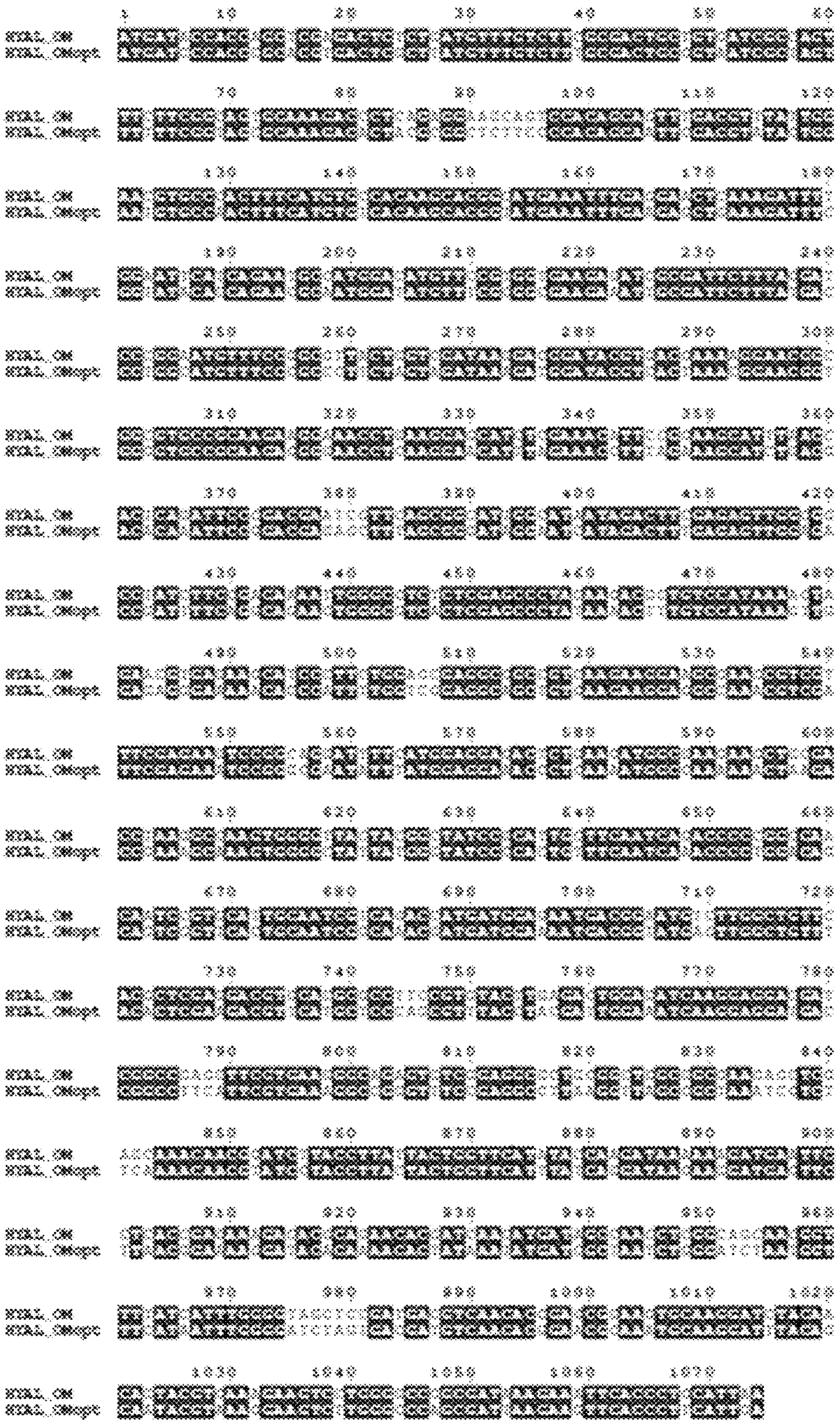
FIG. 1 shows a nucleotide sequence comparison of the codon-optimized hyaluronic acid hydrolase gene and the wild-type gene.

The present application will be further described below in conjunction with the examples, and it should be understood that the examples are only used to further illustrate and explain the present application, and are not intended to limit the present application.

Unless otherwise defined, related technical and scientific terms in the present description have the same meaning as those commonly understood by one of ordinary skill in the art. Although methods and materials similar or identical to those described herein may be used in experiments or practical applications, the materials and methods are described below. In case of conflict, the present description, including definitions therein, shall prevail. In addition, the materials, methods and examples are illustrative and not restrictive. The present application is further described below in conjunction with specific examples, but is not intended to limit the scope of the present application.

As used herein, the term "gene" or "coding sequence" refers to a nucleotide sequence in vitro or in vivo that encodes a gene product. In some instances, the gene consists of or essentially consists of coding sequence, that is, a sequence that encodes the gene product. In other instances, the gene comprises additional, non-coding, sequence. For example, the gene may or may not include regions preceding and following the coding region, e.g., 5' untranslated (5' UTR) or "leader" sequences and 3' UTR or "trailer" sequences, as well as intervening sequences (introns) between individual coding segments (exons).

As used herein, the terms "polypeptide", "peptide", and "protein" are used interchangeably herein to mean a polymer of amino acid residues. That is, the description for the polypeptide is also applicable to the peptide and protein, and vice versa. The terms apply to a natural amino acid polymer and an amino acid polymer in which one or more amino acid residues are non-naturally encoded amino acids. As used herein, the terms encompass amino acid chains of any length.

As used herein, the term "polynucleotide" or "nucleotide" means a single-stranded or double-stranded deoxyribonucleotide, deoxyribonucleoside, ribonucleoside or ribonucleotide and polymers thereof. Unless specifically limited, the terms cover nucleic acids containing known analogs of natural nucleotides that have binding properties similar to reference nucleic acids and are metabolized in a manner similar to naturally occurring nucleotides. Unless otherwise limited specifically, the terms also mean oligonucleotide analogs, including PNAs (peptide nucleic acids), DNA analogs used in antisense techniques (phosphorothioate, phosphoramidate, etc.), etc. Unless otherwise specified, a particular nucleic acid sequence also implicitly encompasses its conserved modified variants (including, but not limited to, degenerate codon substitutions) and complementary sequences as well as explicitly specified sequences.

As used herein, the term "vector" is used to describe a nucleic acid molecule that may be engineered to contain a cloned polynucleotide or polynucleotides that may be amplified in a host cell. Vectors include, but are not limited to, nucleic acid molecules that are single-stranded, double-stranded, or partially double-stranded; nucleic acid molecules that comprise one or more free ends, or no free ends (e.g. circular); nucleic acid molecules that comprise DNA, RNA, or both; and other varieties of polynucleotides known in the art. One type of the vector is a "plasmid", which refers to a circular double-stranded DNA loop into which additional DNA segments can be inserted, such as by standard molecular cloning techniques. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operably linked. Such vectors are referred to herein as "expression vectors." Recombinant expression vectors can comprise a nucleic acid of the present application in a form suitable for expression of the nucleic acid in a host cell, which means that the recombinant expression vectors include one or more regulatory elements, which may be selected on basis of the host cells to be used for expression, that is operably linked to the nucleic acid sequence to be expressed.

As used herein, codon optimization refers to a process of modifying a nucleic acid sequence for enhanced expression in the host cells by replacing at least one codon of the naturalsequence with codons that are more frequently or most frequently used in the genes of that host cell while maintaining the natural amino acid sequence. Various species exhibit particular bias for certain codons of a particular amino acid. Codon bias (differences in codon usage between organisms) often correlates with the efficiency of translation of messenger RNA (mRNA), which is in turn believed to be especially dependent on the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Codon optimization can be achieved, for example, by transforming nucleotide sequences of one species into the genetic sequence of a different species. Optimal codons help to achieve faster translation rates and high accuracy. As a result of these factors, translational selection is expected to be stronger in highly-expressed genes. However, while optimal codon usage is contemplated herein for expression of disclosed proteins, all possible codons are contemplated for use herein for nucleic acids encoding any disclosed protein.

As used herein, the term "signal peptide" means a short peptide (usually 16-30 amino acids) present at the N-terminus of the majority of newly synthesized proteins that are destined to enter the secretory pathway. It may also be referred to as signal sequence, targeting signal, localization signal, localization sequence, transit peptide, leader sequence or leader peptide. The signal peptide is normally cleaved off from the protein by a signal peptidase.

Specifically, firstly, for the full-length gene sequence of hyaluronic acid hydrolase of odontomachusmonticola, thecodon optimizationisperformed according to the codon preference of *Pichia pastoris* to obtain a codon-optimized hyaluronic acid hydrolase gene, the sequence of which is shown in SEQ ID NO. 1. The protein sequence encoded by it is shown in SEQ ID NO. 2, which is consistent with the amino acid sequence encoded by the hyaluronic acid hydrolase gene of the wild-type odontomachusmonticola. Further, a segment of a signal peptide sequence (SEQ ID NO.3) is truncated at the N-terminus of the codon-optimized hyaluronic acid hydrolase gene to obtain the gene for highly expressing hyaluronic acid hydrolase of the present application, the sequence of which is shown in SEQ ID NO.4, and the protein sequence encoded by it is shown in SEQ ID NO.5. Removing the nucleotide sequence shown in SEQ ID NO.3 from the N-terminus of the codon-optimized hyaluronic acid hydrolase gene as shown in SEQ ID NO.1 does not cause translation frameshift, hyaluronic acid hydrolase can be expressed and the expression level and/or enzymatic activity of the recombinant hyaluronic acid hydrolase can be significantly improved. The method fortruncating the signal peptide at the N-terminus may be any method known in the art.

The hyaluronic acid hydrolase of odontomachusmonticola belongs to the third type of hyaluronidase which is endo-β-N-acetylglucosaminidase, and can hydrolyze the β-1,4glycosidic bond of hyaluronic acid to produce the final product having a reducing end of N-acetylglucosamine. In addition, this type of enzyme has a wider substrate spectrum compared with the second type of hyaluronic acid hydrolase of leech, and also has a certain catalytic activity on the structures of chondroitin, chondroitin sulfate and dermatan sulfate. The hyaluronic acid hydrolase of odontomachusmonticola can enrich the types of hyaluronic acid hydrolysates, and may have a wider range of applications than hyaluronidase catalysis.

*Pichia pastoris* is a type of yeast in methylotrophic yeast that can utilize methanol as the sole carbon source and energy source. Like other yeasts, it mainly exists in the form of haploid in the asexual growth phase. When the environmental nutrition is limited, two zygotic haploid cells with different physiological types are often induced to mate and fuse into a diploid. Another biological feature of *Pichia pastoris* is that the alcohol oxidase required for methanol metabolism is sorted into the peroxisome, resulting in regionalization. When glucose is used as carbon source, there are only one or a few small peroxisomes in the thalluses, while when methanol is used as carbon source, peroxisomes account for almost 80% of the entire cell volume, and AOX increases to 35%-40% of total cell protein. Therefore, when the foreign protein gene is inserted by homologous recombination in front of the AOX gene, a large amount of expression can be obtained. At the same time, according to the characteristics of methanol yeast that can form peroxisomes, this system may be used to express some toxic proteins and easily degraded enzymes, and may also be used to study the biogenesis of cell-specific regionalization and its mechanism and function, providing inspiration for similar studies in higher animals.

As shown in FIG. 1, the sequence homology between the optimized hyaluronic acid hydrolase gene of odontomachusmonticola and the wild-type gene is 73.2%.

The present application also provides a recombinant expression vector comprising the nucleotide sequence of the present application. Further, the backbone of the recombinant expression vector is the *Pichia pastoris* vector of pPIC series or pGAP series or pAO815, preferably the vector pPIC9K. The *Pichia pastoris* vector pPIC series includes pPIC9K, pPIC3.5K, pPICZαA,B,C, pPIC9K-His, pPICZA, B,C, etc, with the alcohol oxidase gene promoter PAOX1 as the promoter. The *Pichia pastoris* vector of pGAP series includes pGAPZaA, pGAPZaB, pGAPZaC, pGAPZA, pGAPZB, pGAPZC, etc., with the glyceraldehyde-3-phosphate dehydrogenase promoter PGAP as the promoter. The vector pPIC9K is a *Pichia pastoris* protein expression vector. The kana resistance gene exists in the pPIC9K vector, which allows the use of kana resistance to screen polyclonal copies in yeast. The rest of the vector is exactly the same as the pPIC9 vector. The host bacteria of *Pichia pastoris* that may be used with the pPIC9K vector include a strain of KM71, GS115 or SMD1168.

The present application also provides a *Pichia pastoris* comprising the above-mentioned expression vector, that is, an expression vector comprising the nucleotide sequence as shown in SEQ ID NO.4.

The present application also provides a method for expressing the hyaluronic acid hydrolase gene of the present application, comprising the step of:

producing the hyaluronic acid hydrolase byusing a recombinant *Pichia* pastorisstrain containing the hyaluronic acid hydrolase gene of the present application or the *Pichia* pastorisprovided by the present application.

In a specific embodiment, the method comprises producing the hyaluronic acid hydrolase through fermentation by BMMY medium and methanolinduction.

The composition of the BMMY medium is yeast extract 10 g/L, peptone 20 g/L, $K_2HPO_4$3 g/L, $KH_2PO_4$ 11.8 g/L, YNB 3.4 g/L, ammonium sulfate 10 g/L, biotin $4\times10^{-4}$ g/L, and methanol 10 mL/L. In a preferred embodiment, conditions of the fermentation are as follows: the fermentation temperature is 25° C.-30° C., and 0.5%-1% (v/v) methanol is supplemented every 24 hours during fermentation process toinduceexpression for 96 hours.

In a more preferred embodiment, the recombinant *Pichia* pastoris*P. pastoris* GS115/pPIC9K-AN24HYAL OM$^{opt}$ containing the hyaluronic acid hydrolase gene of the present application is used as a production straionto produce the hyaluronic acid hydrolase by fermentation. The specific fermentation conditions are as follows:

*P. pastoris* GS115/pPIC9K-AN24HYAL_OM$^{opt}$ is inoculated in 40 mL of YPD medium, cultured at 30° C. for 24 hours, and then the seed culture solution is inoculated into 40 mL of BMGY medium at 10% of the inoculumamount for 24 hours of culture. The thalluses arecentrifuged, washed, and transferred to the induction medium BMMY, and 1% (v/v) methanol is supplemented every 24 hours to induce expression for 96 hours.

The present application also provides another method for expressing the hyaluronic acid hydrolase gene of the present application, comprising the following steps:

*Pichia pastoris* is inoculated into a seed medium to obtain a seed liquid;

the seed liquid is inoculated into the BSM fermentation medium for fermentation to obtain a fermentation broth containing hyaluronic acid hydrolase, wherein the fermentation process sequentially includes four stages: initial fermentation, feeding, starvation culture, and methanol induction.

The composition of BSM medium is glycerol 40 g/L, $K_2SO_4$18 g/L, KOH 4.13 g/L, 85% $H_3PO_4$ 26.7 mL/L, $CaSO_4 \cdot 2H_2O$ 0.93 g/L, $MgSO_4 \cdot 7H_2O$ 14.9 g/L, and filter-sterilized PTM14.4 mL/L. The formula of PTM1 is: $CuSO_4 \cdot 5H_2O$ 6 g/L, KI 0.09 g/L, $MnSO_4$ $H_2O$ 3 g/L, $H_3BO_3$ 0.02 g/L, $MoNa_2O_4 \cdot 2H_2O$ 0.2 g/L, $CoCl_2 \cdot 6H_2O$ 0.92 g/L, $ZnCl_2$ 20 g/L, $FeSO_4 \cdot 7H_2O$ 65 g/L, biotin 0.2 g/L, and $H_2SO_4$ 5.0 mL.

In the first stage of initial fermentation, the fermentation temperature is 25° C.-30° C., and the pH is 5-7. The pH is controlled by automatic addition of ammonia water.

In the second stage of feeding, after the glycerol in the BSM medium is exhausted, the batch feeding stage is entered, and 50% (v/v) glycerol (containing 12 mL/L PTM1) is supplemented by exponential feeding, while the rotation speed is set to couple with dissolved oxygen DO. In a preferred embodiment, the feeding rate is 13.5 mL/h/L, 16.2 mL/h/L, 19.2 mL/h/L, 22.8 mL/h/L, 27.2 mL/h/L and 32.4 mL/h/L respectively for the first 6 hours, and is set to 30 mL/h/L for the following 6 hours.

In the third stage of starvation culture, starvation culture is performed for 2-3 hours until the residual glycerol is exhausted, wherein the starvation culture is to study the effect of a single factor on the growth of microorganisms or the production of metabolites, the cells that have been cultured to a certain stage are separated from the medium, and cultured for a certain period of time without the nutrient matrix to exhaust endogenousnutrients accumulated in the cells.

In the fourth stage of methanol induction, the methanol induction is performed at a temperature of 25° C.-30° cfor 80-120 hours.

In a preferred embodiment, pure methanol containing 12 mL/L PTM1 is fed with the final concentration maintained at 1.8% (v/v), while the fermentation temperature is adjusted to 25° C., the rotation speed is increased to 1000 rpm, and the feeding rate of the methanol and the final concentration of the methanol in the medium are controlled online in real time by a methanol detector.

The method of the present application further includes further purifying the above-mentioned fermentation broth.

In a preferred embodiment, the hyaluronic acid hydrolase protein is purified by affinity chromatography using nickel column media and gradient elution using 100-500 mM imidazole buffer.

The enzymatic activity characterization of the hyaluronic acid hydrolase produced by fermentation is determined by the plate transparent circle method, and the enzymatic activity of the fermentation broth supernatant is determined by the 3,5-dinitrosalicylic acid method (DNS).

The definition of activity unit (U) of hyaluronic acid hydrolase is as follows: the amount of enzyme required to release 1 μg glucose reducing equivalent of reducing sugar from hyaluronic acid sugar chain per hour at pH 5.5 and 38° C.

DNS reducing sugar assay: the hyaluronic acid hydrolase of odontomachusmonticola hydrolyzes the β-1,4glycosidic bond of hyaluronic acid to produce a reducing sugar product with a hydroxyl group at the reducing end. The amount of reducing sugar product relative to glucose reducing equivalents produced by hydrolysis of hyaluronic acidic measured by the DNS reducing sugar method, to calculate the catalytic activity of hyaluronic acid hydrolase.

The present application also provides use of the protein as shown in SEQ ID NO. 5 in the preparation of hyaluronic acid-containing adjuvants, foods and cosmetics.

EXAMPLE

Example 1 Construction Ofan Expression System Containing Codon-Optimized Hyaluronic Acid Hydrolase Gene (HYAL_OM$^{opt}$)

Based on the f full-length gene sequence of hyaluronic acid hydrolase ofodontomachusmonticola (Genbank: FX985505.1) published in the NCBI database, the codon optimization was carried out according to the codon preference of *Pichia pastoris*. As shown in FIG. 1, the optimized gene sequence is shown in SEQ ID NO. 1, and has73.2% homology with the sequence of wild-type gene. The amino acid sequence encoded by the optimized gene is shown in SEQ ID NO. 2, which is consistent with the amino acid sequence encoded by the wild-type gene. The codon-optimized sequence of hyaluronic acid hydrolase of odontomachusmonticola was entrusted to Nanjing GenScript Biotechnology Co., Ltd. for whole gene synthesis, and cloned into the expression vector of *Pichia pastoris* pPIC9K between the EcoRI and NotIenzyme cutting sites to obtain recombinant expression Vector pPIC9K-HYAL_OM$^{opt}$. The recombinant sequence was correct after DNA sequencing and comparison. The recombinant expression plasmid pPIC9K-HYAL_OM$^{opt}$ was linearized by SalIfast cutting enzymeand then electro-transformed into *P. pastoris* GS115 expressing host cells. The recombinant transformants were screened by Geneticin G418 to obtain high-copy recombinant *Pichia* pastorisP. *pastoris* GS115/pPIC9K-HYAL OMop.

Example 2 Construction of an Expression System Containing the Gene for Highly Expressing Hyaluronic Acid Hydrolase (AN24HYAL_OM$^{opt}$)

Using the above-mentioned pPIC9K-HYAL_OM$^{opt}$ recombinant expression vector as a template, primers were designed.A segment of the signal peptide sequence at the N-terminus of the full-length hyaluronic acid hydrolase gene was truncatedto obtain a genetically engineered hyaluronic acid hydrolase gene fragment.

The primer sequences are as follows:

```
Upstream primer F:
                                    (SEQ ID NO. 6)
5'-CCGGAATTCATGAAGACACTACGCGGCTC-3';

Downstream primer R:
                                    (SEQ ID NO. 7)
5'-ATTTGCGGCCGCTCAATGATGATGATGGTGGT

GATGAAGGGTGAACTTCTT-3';
```

It should be noted that the GAATTC sequence in the upstream primer is the introduced EcoRI restriction enzyme cutting site, the GCGGCCGC sequence in the downstream primer is the introduced NotI restriction enzyme site, and the reverse complementary sequence of the ATGATGATGATGGTGGTG (positions 16-33 of SEQ ID NO: 7) sequence in the downstream primer encodes 6×His-tag tags.

The amplified genetically engineered hyaluronic acid hydrolase gene fragment was subjected to EcoRI and NotI double enzyme digestion, thencloned into the linear expression vector pPIC9K treated with the same digestion, and transformed into E.coil TOP10. The recombinant expression plasmid pPIC9K-AN24HYAL_OM$^{opt}$ was obtained under the premise of no frameshifting, and the recombinant sequence was correct after DNA sequencing and comparison. The recombinant plasmid was linearized by restriction endonuclease SalI and then electro-transformed into *P. pastoris* GS115 cells. The recombinant transformants were screened by Geneticin G418 to obtain the recombinant strain *P. pastoris* GS115/pPIC9K-AN24HYAL_OM$^{opt}$ with high-copy hyaluronic acid hydrolase gene.

Example 3 Heterologous Expression of Hyaluronic Acid Hydrolase by Recombinant *Pichia pastoris*

The obtained recombinant engineering strainP. *pastoris* GS115/pPIC9K-HYAL_OM$^{opt}$ and *P. pastoris*GS115/pPIC9K-AN24HYAL_OM$^{opt}$ were respectively subjected to shake flask fermentation culture. The fermentation steps were as follows: a single clone was picked, inoculated in 40 mL of YPD medium (yeast extract 10 g/L, peptone 20 g/L, glucose 20 g/L), and cultured at 30° C.,200 rpm for 24 hours. It was transferred to 40 mL of initial expression medium BMGY (yeast extract 10 g/L, peptone 20 g/L, $K_2HPO_4$ 3 g/L, $KH_2PO_{411.8}$ g/L, YNB 3.4 g/L, ammonium sulfate 10 g/L, biotin $4\times10^{-4}$ g/L, glycerol 10 mL/L) at 10% inoculum amount, and cultured at 30° C.,200 rpm for 24 hours. The thalluses were collected by centrifugation, washed with normal saline, and then changed to 40 mL of induction expression medium BMMY (yeast extract 10 g/L, peptone 20 g/L, $K_2HPO_43$ g/L, $KH_2PO_411.8$ g/L, YNB 3.4 g/L, ammonium sulfate 10 g/L, biotin $4\times10^{-4}$ g/L, methanol 10 mL/L) for culture, pure methanol was added to the medium every 24 hours to a final concentration of 1.0% (v/v) to induce expression for 96 hours.

Figure 2:
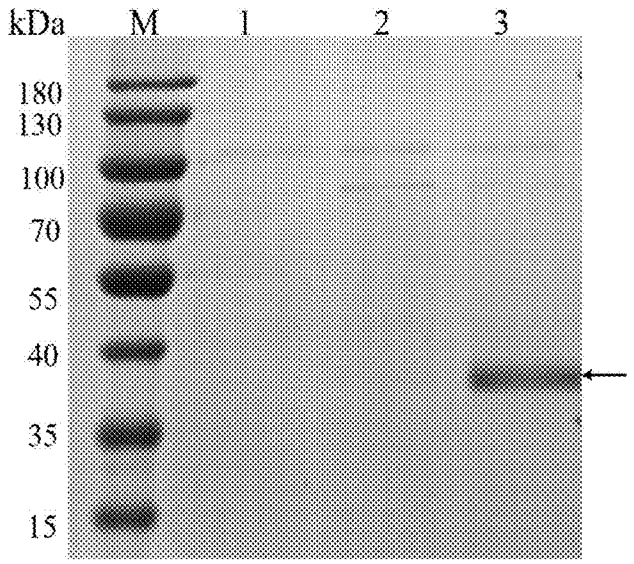
FIG. 2 shows the SDS-PAGE graph of the fermentation supernatant of recombinant hyaluronic acid hydrolase, wherein lane M represents the standard protein with a molecular weight of 180 kDa; lane 1 represents the fermentation supernatant of recombinant strain *P. pastoris* GS115/pPIC9K (negative control); lane 2 represents the fermentation supernatant of codon-optimized recombinant strain *P. pastoris* GS115/pPIC9K-HYAL_OM$^{opt}$ (positive control); and lane 3 represents the fermentation supernatant of the recombinant strain *P. pastoris* GS115/pPIC9K-AN24HYAL OM$^{opt}$ constructed in the present application.

The fermentation supernatant was detected by SDS-PAGE protein electrophoresis, and the results are shown in FIG. 2. Compared with the recombinant strain in lane 2 (the recombinant strainP. *pastoris* GS115/pPIC9K-HYAL_OM$^{opt}$ containing the full-length hyaluronic acid hydrolase gene sequence), there is an obvious protein band (indicated by the arrow) at the theoretical molecular weight of about 39 kDa, indicating that the recombinase has achieved efficient secretion expression after truncation of its signal peptide sequence.

Figure 3:
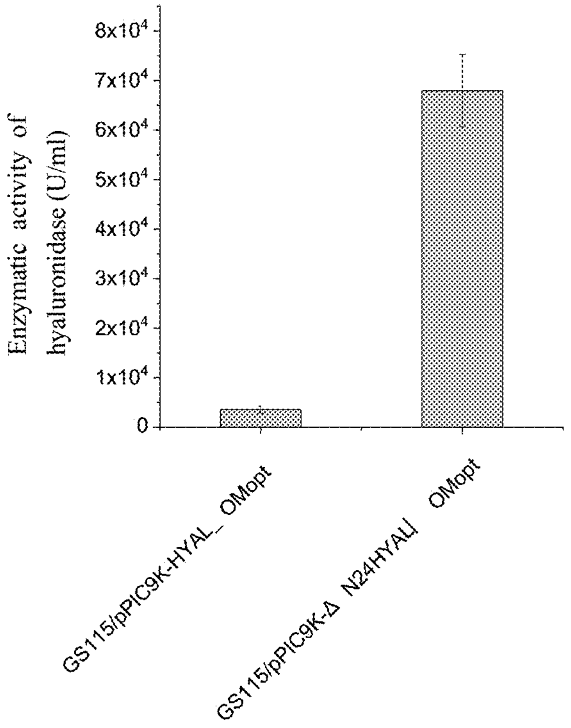
FIG. 3 shows the crude enzymatic activity of the fermentation supernatant of the codon-optimized recombinant strain *P. pastoris* GS115/pPIC9K-HYAL_OM$^{opt}$ and the recombinant strain *P. pastoris* GS115/pPIC9K-AN24HYAL_OM$^{opt}$ constructed in the present application as determined by DNS method.

Example 4Enzymatic Activity Detection of Shake Flask Fermentation Supernatant of the Recombinant Strain The reducing sugar equivalent produced by the hydrolysis of hyaluronic acid was determined by DNS method, and the activity of hyaluronic acid hydrolase was calculated by standard curve with analytically pure glucose. 1 mL of reaction system: 10 μL of fermentation supernatant (the boil-inactivated fermentation supernatant with an equal volume was used as the blank) and 190 μL of 50 mM citric acid buffer (pH 5.5) were added to 800 μL of 2 mg/mL hyaluronic acid substrate solution, and incubated at 38° C. for 15 min.After the reaction, the mixture was immediately placed in a boiling water bath for 2 min to inactivate the enzyme to terminate the reaction. The treated 1 mL reaction solution was added to 2 mL DNS (potassium sodium tartrate tetrahydrate 248 g/L, 3,5-dinitrosalicylic acid 6.3 g/L, 2M NaOH 250 mL/L, phenol 5.136 g/L, sodium sulfite 5 g/L) solution. The obtained mix was shakedto mix well, subjected for boiling water bath togetherwith the glucose standard curve sample for 10 min, and then cooled to room temperature in an ice bath. 7 mL of deionized water was added and shaking was performed to mix well. The absorbance was measuredat 540 nm, and converted into the amount of reducing sugar produced by the reaction. The crude enzymatic activity of the fermentation supernatant of the recombinant engineering strain was calculated according to the glucose standard curve. The results are shown in FIG. 3, the enzymatic activity of the fermentation supernatant of the recombinant strain *P. pastoris* GS115/pPIC9K-HYAL_OM$^{opt}$ constructed by the present application is 3547.88 U/mL, and the enzymatic activity of the fermentation supernatant of the recombinant strain *P. pastoris* GS115/pPIC9K-AN24HYAL_OM$^{opt}$ reaches 67970.04U/mL.

Example 5 High-Density Culture of Recombinant Strains in a5-L Fermenter

The recombinant strain *P. pastoris* GS115/pPIC9K-AN24HYAL_OM$^{opt}$ was subjected to high density culture in a 5-L fermentor. The single colony on the YPD plate was transferred to 50 mL of YPD liquid medium, cultured at 220 rpm, 30° C. for 24 hours, and the culture solution was inoculated into 200 mL of BMGY medium at 10%, and cultured at 30° C., 220 rpm for 24 hours. The 200 mL seed solution cultured for 24 hours was added into a 5-L fermenter containing 2 L BSMfermentation medium (glycerol 40 g/L, $K_2SO_4$ 18 g/L, KOH 4.13 g/L, 85% $H_3PO_4$ 26.7 mL/L, $CaSO_4\cdot2H_2O$ 0.93 g/L, $MgSO_4\cdot7H_2O$ 14.9 g/L, filter-sterilized PTM14.4 mL/L;the formula of PTM1 is: $CuSO_4$: $5H_2O$ 6 g/L, KI 0.09 g/L, $MnSO_4$ $H_2O$ 3 g/L, $H_3BO_3$ 0.02 g/L, $MoNa_2O_4$: $2H_2O$ 0.2 g/L, $CoCl_2$: $6H_2O$ 0.92 g/L, $ZnCl_2$ 20 g/L, $FeSO_4\cdot7H_2O$ 65 g/L, biotin 0.2 g/L, $H_2SO_4$ 5.0 mL).

The initial fermentation parameters were set as temperature of 30° C., pH of 5.5, aeration volume of 2.0vvm and rotation speed of 500 rpm. During the fermentation process, the pH was controlled at 5.5 by automatically adding ammonia water. After the glycerol in the BSM medium was exhausted, the batch feeding stage was entered. 50% (v/v) glycerol (containing 12 mL/L PTM1) was supplemented by exponential feeding, while the rotation speed was set to couple with dissolved oxygen DO. The feeding rate was 13.5 mL/h/L, 16.2 mL/h/L, 19.2 mL/h/L, 22.8 mL/h/L, 27.2 mL/h/L and 32.4 mL/h/L respectively for the first 6 hours, and is set to 30 mL/h/L for the following 6 hours. After the feeding, the stage of starvation culture was entered. The starvation culture was performed for 2-3 hours until the residual glycerol was exhausted. The stage of methanol induction was entered. The pure methanol containing 12 mL/L PTM1 was fed with the final concentration maintained at 1.8% (v/v), while the fermentation temperature was adjusted to 25° C., the rotation speed was increased to 1000 rpm, and the feeding rate of the methanol and the final concentration of the methanol in the medium were controlled online in real time by a methanol detector. After entering the stage of methanol induction, samples were taken at regular intervals to detect the enzymatic activity of the fermentation supernatant.

Figure 4:
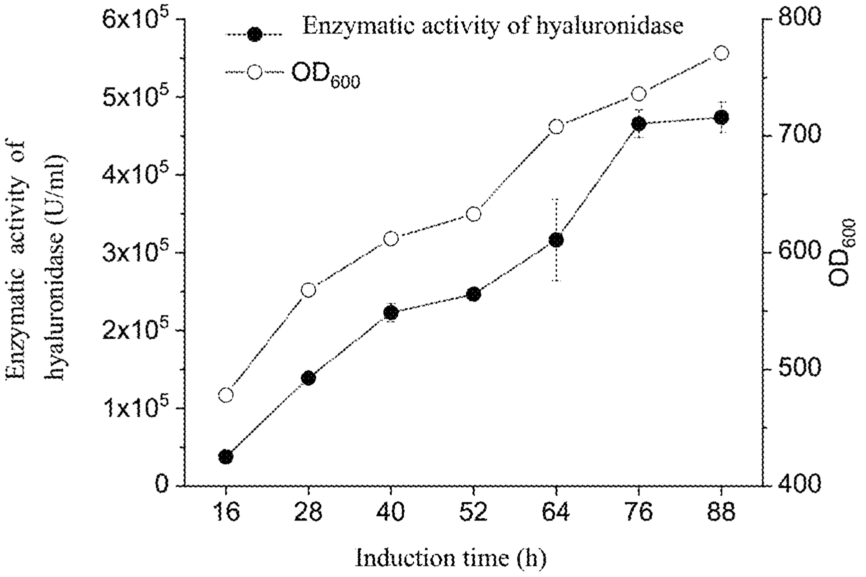
FIG. 4 shows the biomass and enzymatic activity curves of recombinant strain *P. pastoris* GS115/pPIC9K-AN24HYAL_OM$^{opt}$ cultured at high density in a 5-L fermenter.

The detection results of enzymatic activity are shown in FIG. 4. When methanol induction is performed for 88 hours, the highest enzymatic activity of hyaluronic acid hydrolase in the fermentation supernatant is $4.7\times10^5$U/mL. The enzymatic activity or protein expression level obtained by high-density fermentation is 6.97 times that of shake flask fermentation, making it possible for industrial production.

Example 6 Purification of Genetically Engineered Hyaluronic Acid Hydrolase

Figure 5:
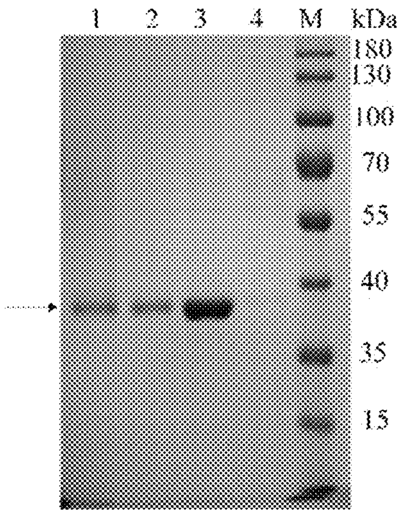
FIG. 5 shows the SDS-PAGE graph of the fermentation supernatant of recombinant strain *P. pastoris* GS115/pPIC9K-AN24HYAL_OM$^{opt}$ after gradient elution with imidazole buffer of different concentrations, wherein lane M represents the standard protein with a molecular weight of 180 kDa; and lanes 1-4 represent imidazole concentrations of 100 mM, 200 mM, 300 mM, and 500 mM, respectively.

Six polyhistidine purification tags were introduced at the C-terminus of the genetically engineered hyaluronic acid hydrolase, and could specifically bind to nickel ions to purify the protein. Firstly, the nickel column media was filled into an affinity chromatography column, and then the nickel column was activated with 5 column volumes of binding buffer (20 mM sodium phosphate, 0.5 NaCl, 20 mM imidazole, pH 6.0). An appropriate amount of ultrafiltration concentrated fermentation supernatant filtered through 0.22 μm was added, impurities were eluted with 5 column volumes of binding buffer, and then the target protein was gradient eluted with 10 column volumes of elution buffer having 100 mM, 200 mM, 300 mM, and 500 mM imidazole, respectively. The eluent was verified by SDS-PAGE, and the results are shown in FIG. 5. Lane 3 is the protein band byelution with 300 mM imidazole buffer, with the highest protein concentration and a single band. The obtained pure protein of genetically engineered hyaluronic acid hydrolase has normal hyaluronic acid hydrolase activity by enzymatic activity assay.

Sequence listing

```
SEQ ID NO. 1:
atgatcccacccgcacgtgactcgcttatgtttgtctttgcgactgcggtaatcgctagt     60
tttttcggtagcgcaaagacactacgcggctcttccccacagcaattcgacgtatactgg    120
aatgtgccaactttcatgtgtcacaagcacggtatgaaatttgaagagctgaaagatttc    180
ggtatacaccagaacgcaatggatatgtttcgcggcgaagaaattgcgattctttatgac    240
cctggcatgtttcccgcccttctagtagataaagatggatacgtcactaaacggaacggt    300
ggggtgccgcaagaggggaacctcaaggaacatttagaaacctttagaaagcatctgacg    360
acacaaattccggacgagagctttagcgggataggaatcatagactttgagagttggaga    420
ccgattttcaggcagaactgggcgtcactcgagccctataaaactttgtccataaagttg    480
gagagggaaaaacacccatttggtcggaggcagctgtgaagaaggaggccaaacgtcga     540
ttcgagaaatccgggcgaatatttatggaggaaaccctcaaaatggccaaaaaactaaga    600
ccgaaagcaaagtggggctattatgggtatccccactgtttcaatcaaacccctggacag    660
cagtcggttcactgcaatcggcaaacgatgatggaaaatgacggtatgagttggctgttt    720
acactcgaagacgttcatgctcccagcgtttacctacgattggaaatcaaggaggatgac    780
cggccttcattcgtgaaaggccgggtttccgaggccttaaggttagccgctaaatcgtct    840
tcaaaacaacgtatcctaccttactactggttcatttatcaggataagaaggatgagttc    900
ttaacggaaaaggatacacaaaacactataaatatgatcgctaatctgggatctaatggt    960
ttcataatttggggatctagtgacgatgtcaacacggaacgcaaatgcaaggatttacag   1020
caatacgtaaaggaagtcttgggcccagcgattaagaagttcacccttcattga         1074

SEQ ID NO. 2:
Met Ile Pro Pro Ala Arg Asp Ser-
Leu Met Phe Val Phe Ala Thr Ala
1                5                 10                15
Val Ile Ala SerPhePheGlySer Ala Lys ThrLeuArgGlySerSer
            20                25                30
Pro GlnGlnPhe Asp Val Tyr TrpAsn Val Pro ThrPhe Met Cys His
         35                40                45
Lys His Gly Met Lys PheGluGluLeu Lys Asp PheGly Ile His Gln
     50                55                60
Asn Ala Met Asp Met PheArgGlyGluGlu Ile Ala Ile Leu Tyr Asp
65               70                75                  80
Pro Gly Met Phe Pro Ala Leu-
Leu Val Asp Lys Asp Gly Tyr Val Thr
            85                90                95
Lys ArgAsnGlyGly Val Pro GlnGluGly AsnLeu Lys Glu His Leu
          100               105               110
GluThrPheArg Lys His LeuThrThrGln Ile Pro Asp GluSerPhe
          115               120               125
SerGly Ile Gly Ile Ile Asp PheGluSerTrpArg Pro Ile PheArg
    130               135               140
GlnAsnTrp Ala SerLeuGlu Pro Tyr Lys ThrLeuSer Ile Lys Leu
145              150               155                 160
```

-continued

Sequence listing

```
GluArgGlu Lys His Pro PheTrpSerGlu Ala Ala Val Lys LysGlu
               165                 170                 175
Ala Lys ArgArgPheGlu Lys SerGly Arg Ile Phe Met GluGluThr
        180                 185                 190
Leu Lys Met Ala Lys LysLeuArg Pro Lys Ala Lys TrpGly Tyr Tyr
       195                 200                 205
Gly Tyr Pro His CysPheAsnGlnThr Pro GlyGlnGlnSer Val His
    210                 215                 220
CysAsnArgGlnThr Met MetGluAsn Asp Gly Met SerTrpLeuPhe
225                 230                 235                 240
ThrLeuGlu Asp Val His Ala Pro Ser Val Tyr LeuArgLeuGlu Ile
               245                 250                 255
Lys Glu Asp AspArg Pro SerPhe Val Lys Gly Arg Val SerGlu Ala
           260                 265                 270
LeuArgLeu Ala Ala Lys SerSerSer Lys GlnArg Ile Leu Pro Tyr
        275                 280                 285
Tyr TrpPhe Ile Tyr Gln Asp Lys Lys Asp GluPheLeuThrGlu Lys
      290                 295                 300
Asp ThrGlnAsnThr Ile Asn Met Ile Ala AsnLeuGlySerAsnGly
305                 310                 315                 320
Phe Ile IleTrpGlySerSer Asp Asp Val AsnThrGluArg Lys Cys
               325                 330                 335
Lys Asp LeuGlnGln Tyr Val Lys Glu Val LeuGly Pro Ala Ile Lys
           340                 345                 350
Lys PheThrLeu His
      355

SEQ ID NO. 3
atcccacccgcacgtgactcgcttatgtttgtctttgcgactgcggtaatcgctagtttt     60
ttcggtagcg ca                                                    72

SEQ ID NO. 4
atgaagacactacgcggctcttccccacagcaattcgacgtatactggaatgtgccaact     60
ttcatgtgtcacaagcacggtatgaaatttgaagagctgaaagatttcggtatacaccag    120
aacgcaatggatatgtttcgcggcgaagaaattgcgattctttatgaccctggcatgttt    180
cccgcccttctagtagataaagatggatacgtcactaaacggaacggtggggtgccgcaa    240
gaggggaacctcaaggaacatttagaaacctttagaaagcatctgacgacacaaattccg    300
gacgagagctttagcgggataggaatcatagactttgagagttggagaccgattttcagg    360
cagaactgggcgtcactcgagccctataaaactttgtccataaagttggagagggaaaaa    420
cacccattttggtcggaggcagctgtgaagaaggaggccaaacgtcgattcgagaaatcc    480
gggcgaatatttatggaggaaaccctcaaaatggccaaaaaactaagaccgaaagcaaag    540
tggggctattatgggtatccccactgtttcaatcaaacccctggacagcagtcggttcac    600
tgcaatcggcaaacgatgatggaaaatgacggtatgagttggctgtttacactcgaagac    660
gttcatgctcccagcgtttacctacgattggaaatcaaggaggatgaccggccttcattc    720
gtgaaaggccgggtttccgaggccttaaggttagccgctaaatcgtcttcaaaacaacgt    780
atcctaccttactactggttcatttatcaggataagaaggatgagttcttaacggaaaag    840
gatacacaaaacactataaatatgatcgctaatctgggatctaatggtttcataatttgg    900
ggatctagtgacgatgtcaacacggaacgcaaatgcaaggatttacagcaatacgtaaag    960
gaagtcttgggcccagcgattaagaagttcacccttcatcaccaccatcatcatcattga   1020

SEQ ID NO. 5:
Met Lys ThrLeuArgGlySerSer Pro GlnGlnPhe Asp Val Tyr Trp
1               5                   10                  15
Asn Val Pro ThrPhe Met Cys His Lys His Gly Met Lys PheGluGlu
            20                  25                  30
Leu Lys Asp PheGly Ile His GlnAsn Ala Met Asp Met PheArgGly
        35                  40                  45
GluGlu Ile Ala Ile Leu Tyr Asp Pro Gly Met Phe Pro Ala LeuLeu
    50                  55                  60
Val Asp Lys Asp Gly Tyr Val Thr Lys ArgAsnGlyGly Val Pro Gln
65                  70                  75                  80
GluGly AsnLeu Lys Glu His LeuGluThrPheArg Lys His LeuThr
                85                  90                  95
ThrGln Ile Pro Asp GluSerPheSerGly Ile Gly Ile Ile Asp Phe
           100                 105                 110
GluSerTrp Arg Pro Ile PheArgGlnAsnTrp Ala SerLeuGlu Pro
      115                 120                 125
Tyr Lys ThrLeuSer Ile Lys LeuGluArgGlu Lys His Pro PheTrp
    130                 135                 140
SerGlu Ala Ala Val Lys LysGlu Ala Lys ArgArgPheGlu Lys Ser
145                 150                 155                 160
Gly Arg Ile Phe Met GluGluThrLeu Lys Met Ala Lys LysLeuArg
                165                 170                 175
Pro Lys Ala Lys TrpGly Tyr TyrGly Tyr Pro His CysPheAsnGln
            180                 185                 190
Thr Pro GlyGlnGlnSer Val His CysAsnArgGlnThr Met MetGlu
        195                 200                 205
```

-continued

Sequence listing

```
Asn Asp Gly Met SerTrpLeuPheThrLeuGlu Asp Val His Ala Pro
    210                215                 220
Ser Val Tyr LeuArgLeuGlu Ile Lys Glu Asp AspArg Pro SerPhe
225                230                 235                 240
Val Lys Gly Arg Val SerGlu Ala LeuArgLeu Ala Ala Lys SerSer
                 245                 250                 255
Ser Lys GlnArg Ile Leu Pro Tyr TyrTrpPhe Ile Tyr Gln Asp Lys
            260                 265                 270
Lys Asp GluPheLeuThrGlu Lys Asp ThrGlnAsnThr Ile Asn Met
        275                 280                 285
Ile Ala AsnLeuGlySerAsnGly Phe Ile IleTrpGlySerSer Asp
    290                295                 300
Asp Val AsnThrGluArg Lys Cys Lys Asp LeuGlnGln Tyr Val Lys
305                310                 315                 320
Glu Val LeuGly Pro Ala Ile Lys LysPheThrLeu His HisHisHis
                325                 330                 335
His HisHis
```

SEQ ID NO. 6:
CCGGAATTCATGAAGACACTACGCGGCTC

SEQ ID NO. 7:
ATTTGCGGCCGCTCAATGATGATGATGGTGGTGATGAA GGGTGAACTTCTT

The invention claimed is:

1. A gene for efficiently expressing hyaluronic acid hydrolase, comprising the nucleotide sequence of SEQ ID NO: 4.

2. A protein encoded by the gene of claim 1, comprising the amino acid sequence of SEQ ID NO: 5.

3. A recombinant expression vector, comprising the nucleotide sequence of SEQ ID NO: 4.

4. The recombinant expression vector of claim 3, wherein the recombinant expression vector is a *Pichia pastoris* vector of pPIC series, or pGAP series, or pAO815.

5. A *Pichia pastoris*, comprising the expression vector of claim 3.

6. A method for producing hyaluronic acid hydrolase, comprising the step of:

culturing a recombinant *Pichia pastoris* strain comprising the gene of claim 1, to produce the hyaluronic acid hydrolase.

7. The method of claim 6, wherein the *Pichia pastoris* is a strain of GS115, KM71 or SMD1168.

8. The method of claim 6, wherein the method comprises producing the hyaluronic acid hydrolase through fermentation by Buffered Methanol-complex Medium (BMMY) and methanol induction.

9. The method of claim 8, wherein conditions of the fermentation are as follows: fermentation temperature is 25° C.-30° C., and 0.5%-1% (v/v) methanol is supplemented every 24 hours during the fermentation to induce expression for 96 hours.

10. The method of claim 6, wherein the method comprises producing the hyaluronic acid hydrolase through fermentation by Basal Salt Medium (BSM) and methanol induction.

11. The method of claim 10, wherein the method comprises steps of:

inoculating *Pichia pastoris* into a seed medium to obtain a seed liquid;

inoculating the seed liquid into BSM for fermentation to obtain a fermentation broth containing the hyaluronic acid hydrolase, wherein a fermentation process sequentially comprise four stages: initial fermentation, feeding, starvation culture, and methanol induction.

12. The method of claim 11, wherein conditions of the initial fermentation are as follows: fermentation temperature is 25° C.-30° C., and pH is 5-7.

13. The method of claim 11, wherein a time of the starvation culture is 2-3 hours.

14. The method of claim 11, wherein the methanol induction is performed at a temperature of 25° C.-30° C. for 80-120 hours.

15. The method of claim 11, wherein the method further comprises purifying the fermentation broth.

16. The method of claim 15, wherein the purification is performed by affinity chromatography utilizing nickel column media and gradient elution utilizing 100-500 mM imidazole buffer.

17. The recombinant expression vector of claim 4, wherein the recombinant expression vector is pPIC9K.

* * * * *